Figure 1:
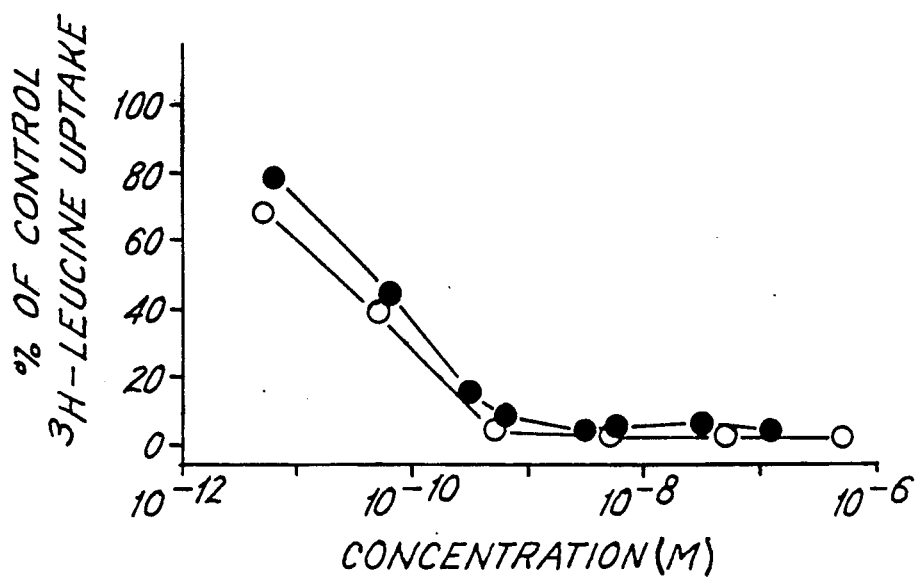

United States Patent [19]

Uhr et al.

[11] Patent Number: 5,045,451

[45] Date of Patent: Sep. 3, 1991

[54] METHODS FOR SCREENING ANTIBODIES FOR USE AS IMMUNOTOXINS

[76] Inventors: Jonathan W. Uhr, Ellen S. Vitetta, both of Dallas, Tex.

[73] Assignee: Board of Regents, Austin, Tex.

[21] Appl. No.: 262,974

[22] Filed: Oct. 26, 1988

[51] Int. Cl.[5] .................. G01N 33/563; G01N 33/567; G01N 33/577

[52] U.S. Cl. ..................................... 435/7.23; 435/29; 435/7.24; 436/503; 436/512; 436/519; 436/547; 436/548; 436/813

[58] Field of Search ...................... 435/7, 29; 436/503, 436/512, 519, 547, 548, 813

[56] References Cited

U.S. PATENT DOCUMENTS

| | | | |
|---|---|---|---|
| 4,360,592 | 11/1982 | Weltman | 435/7 |
| 4,664,911 | 5/1987 | Uhr et al. | 436/512 |
| 4,689,311 | 8/1987 | Weltman | 436/519 |

FOREIGN PATENT DOCUMENTS

WO8701941  4/1987  PCT Int'l Appl.

OTHER PUBLICATIONS

Raso et al., J. Immunol. 125(6): 2610-2616 (1980), "Specific Cytotoxicity of a Human Immunoglobulin-Directed Fab'-Ricin A Chain Conjugate".
Fulton et al., J. Immunol. 136(8): 3103-3109 (1986, "The Effect of Antibody Valency and Lysosomotropic Amines on the Synergy Between Ricin A Chain and Ricin B Chain-Containing Immunotoxins".
Weltman et al., (1987), Can. Res., 47:5552-5556.
Vitetta et al., (1987), Science, 238:1098-1104.
Till et al., (1988), Cancer Res., 48:1119-1123.
Weltman et al., (1986), *BioTechniques,* 4:224-228.

*Primary Examiner*—David A. Saunders

[57] ABSTRACT

The present disclosure described an assay for screening monoclonal antibodies for their potential as highly cytotoxic immunotoxins. The assay involves treating cells with dilutions of the test antibody followed by a Fab fragment of a secondary antibody coupled to an A chain toxin ("indirect assay"). The cytotoxicity of the indirect assay is compared to that of the direct assay where the monoclonal antibody is coupled to an A chain toxin. Indirect and direct assays were carried out using 14 antibodies and a panel of 8 human and mouse cell types. The two assays showed virtually 100% correlation. The indirect assay, therefore, predicts the potency of a given monoclonal antibody to make an effective immunotoxin and should be useful in screening monoclonal antibodies for use as immunotoxins.

10 Claims, 1 Drawing Sheet

METHODS FOR SCREENING ANTIBODIES FOR USE AS IMMUNOTOXINS

BACKGROUND OF THE INVENTION

The government may own certain rights in the present invention pursuant to NIH grants CA-41081 and CA-28149.

1. Field of the Invention

The present invention relates to improved methods for screening antibody populations to select those populations having cytotoxic potential as immunotoxins. In particular aspects, the present invention relates to indirect assays for screening populations of antibodies employing a screening reagent which includes a toxin-linked univalent antibody fragment.

2. Description of the Related Art

In recent years, conjugates of cell-reactive antibodies and the A chains of toxins such as ricin, diptheria toxin and the like, have become increasingly important in medical applications. For example, such conjugates, referred to as immunotoxins, have been used to kill normal and malignant target cells both in vitro (1-4) and in vivo (5-9). Moreover, immunotoxins have been used both experimentally and clinically in the management or treatment of a variety of diseases or disorders, such as the treatment of autoimmune diseases, various malignancies, and even to purge bone marrow of T-cells or tumor cells before transplantation (reviewed in Ref's 10 and 11).

A significant problem, however, in the development of immunotoxins is the finding that not all monoclonal antibodies make highly toxic immunotoxins. Different monoclonal antibodies used as immunotoxins vary over 10,000-fold in their potency as specific cytotoxic reagents (10,11). It appears that some of the factors which determine the potency of an immunotoxin include the cell surface antigen to which the antibody is directed and its resultant pathway of internalization after binding to the immunotoxin (12-14), the density of the cell surface antigen (15-16), the epitope recognized by the antibody, and the affinity of the antibody utilized (17). Furthermore, different cells expressing the same antigenic determinants may vary in their susceptibility to the same immunotoxin (17-19). Because of this complexity, it is difficult to predict whether any given antibody will make an effective immunotoxin.

Based on the results of studies by Bjorn et al. (18), one can estimate that only one in four monoclonal antibodies, at best, is of sufficient potency ($IC_{50}=10^{-11}-10^{-13}M$) to be considered for clinical use as an immunotoxin. Previously, in screening monoclonals for their potential use as immunotoxins, it has been necessary to produce and purify large quantities of monoclonal antibodies, couple them to ricin A chain, and purify the resultant immunotoxin. Each immunotoxin must then be tested for its ability to kill an appropriate target cell. This procedure is laborious, expensive and limits the number of monoclonal antibodies that can be evaluated.

Recently, Weltman et al. (20) described a method for potentially screening large numbers of monoclonal antibodies for their efficacy as immunotoxins. This method, called an "indirect immunotoxin" assay, is similar in some respects to indirect immunofluorescence staining. Target cells are treated with primary (1°) unconjugated monoclonal antibodies, washed, and then incubated with a secondary (2°) toxin-linked immunoglobulin antibody having binding immuno-specificity for the primary antibody.

In the Weltman et al. study (20), this method was used to screen 12 monoclonal antibodies specific for a small cell lung cancer line. One monoclonal antibody was reported to induce significant inhibition of protein synthesis in the cell in the indirect assay. However, the validity, sensitivity and specificity of the approaches employed by Weltman et al. was not shown because none of the antibodies were employed directly as immunotoxins. Furthermore, the design of the assay was seriously flawed—because immunoglobulins are immunologically divalent, it is likely that the primary cell-bound monoclonal antibody is being cross-linked. Cross-linking can alter the route of internalization of monoclonal antibodies and thus significantly alter the toxicity of the toxin-linked secondary antibody (21).

Due to the potential lack of specificity and sensitivity in existing indirect assays, there is presently a need for improved assays for screening antibodies. In particular, there is a need to assays which can predict the usefulness of antibodies in the preparation of immunotoxins which do not present the possibility of inaccuracies due to cross-linking of the primary antibody.

SUMMARY OF THE INVENTION

The present invention addresses at least some of the problems associated with previous indirect screening assays by providing an improved indirect immunotoxin assay in which the secondary toxin-linked reagent comprises a univalent fragment, such as a Fab fragment, instead of a divalent molecule. It is proposed that by employing a univalent fragment, many if not most of the inaccuracies believed to be associated with previous approaches are addressed.

Accordingly, the present invention is directed in a general sense to an improved method for assessing the ability of an antibody to make an effective immunotoxin. The improved method of the present invention includes a step of incubating target cells with a first or primary antibody that is to be tested, under conditions appropriate for immunocomplex formation. Under such conditions, the primary antibody being tested will bind to the target cells where the target cells exhibit a membrane antigen recognized by the test antibody.

Practice of the invention further includes introducing into the incubation mixture a toxin linked to a univalent antibody fragment having binding affinity for the primary antibody. A preferred univalent antibody fragment comprises Fab fragments having binding affinity for the species and class of primary antibody being tested. Thus, for example, where the primary antibody is of mouse derivation, as is often the case in connection with monoclonal antibodies, useful Fab fragments may be obtained by well known techniques from antisera raised against mouse immunoglobulin molecules. Antibodies can also be raised against human Ig, rat Ig, etc.

While a preferred univalent fragment for practice herewith comprises an Fab fragment, other univalent fragments are also envisioned as being useful. For example, Fab' or Fab'Fc fragments can be employed.

The type of toxin or toxin subunit employed will typically be a toxin or other ligand of the sort that will ultimately be employed in connection with the immunotoxin that is being developed. Where one is seeking ultimately to prepare a ricin A-chain linked immunotoxin, one will generally desire to employ a ricin A- chain linked univalent fragment in the practice of the indirect screening assay hereof. However, the invention is not limited to the use of ricin A chain toxins. Other exemplary toxins include A chain toxins in general, such as that of diptheria toxin, abrin, or *Pseudomonas exotoxin*. Other possible ligands include hormones, growth factors, protein A, viral binding proteins, or any other ligand for which a cell expresses a receptor. In such cases, the secondary univalent binding fragment would be directed against another site on the hormone, growth factor, ect.

In preferred aspects, the toxin will be covalently bound to the univalent secondary binding fragment, for example, by a disulfide linkage. However, other means of covalent linkage are known and can be employed where desired. For example, with "blocked" toxins one can use thioether linkages. One could also employ a third binding molecule such as a Protein A-linked toxin, which brings the toxin into association with the target cell.

The target cell employed will, of course, depend on the type of immunotoxin that is being developed. Thus, for example, where one is developing an immunotoxin directed towards a particular tumor antigen, one will desire to employ a cell expressing that target antigen. Where one is developing an anti-B cell or anti-T cell immunotoxin, one will desire to employ, respectively, a target cell which exhibits the B-cell or T-cell antigen. In any event, it is submitted that an appropriate target cell will be apparent to those of skill in the art in light of the present disclosure.

By introducing the toxin-linked univalent fragment into the incubation mixture, the toxin is delivered to the target cell in a manner closely analogous to how it would have been delivered by the primary antibody itself. Thus, the indirect assay of the present invention closely mimics the level of cytotoxicity that would be observed with direct immunotoxin killing.

An additional step of the method of the present invention involves testing for the exertion of a cytotoxic effect upon the target cells by the toxin. The particular testing method will, of course, depend on the particular toxin that is employed in the assay. Thus, where an A chain toxin is employed, one will typically desire to test for the appearance of cytotoxicity related to the inhibition of protein synthesis. A preferred assay in this regard looks generally to an inhibition of protein synthesis, e.g., radioactive leucine incorporation, into protein by the target cell. However, numerous other assays are envisioned as useful in connection with the present invention, and appropriate assays will be apparent to those of skill in the art in light of the present disclosure.

BRIEF DESCRIPTION OF THE DRAWINGS

FIG. 1. Representative experiment showing a comparison of the direct (○) and indirect (●) immunotoxin assay using murine AKR/A cells and OX7 (anti-Thy 1) antibody.

FIG. 2. $IC_{50}$ values for the direct versus indirect immunotoxin assays using Daudi cells and various anti-CD22 (RFB4, UV22-1, UV22-2 and HD6) antibodies (Table 4) or controls (OX7 and MOPC-21). Values were averages of four experiments. (○), RFB4; (●), HD6; (Δ), UV22-2; (▲), UV22-1; (■), MOPC-21 (control) and OX7 (control).

DETAILED DESCRIPTION OF THE PREFERRED EMBODIMENTS

Technical Parameters of the Indirect IT Assay

Several technical parameters were evaluated in order to optimize the indirect immunotoxin assay. The following parameters were found to be important:

(a) it was found to be important to titrate the secondary reagent, i.e., the toxin-linked univalent fragment, against each dilution of a monoclonal antibody known to function effectively as a direct immunotoxin in order to determine the single dilution of the toxin-linked univalent fragment to be routinely used in the indirect immunotoxin assays. The concentration of the toxin-linked univalent fragment (typically 0.5-1 ug/ml) can then be used on any target cell with dilutions of any primary antibody to be tested;

(b) of various times and temperatures of incubation evaluated, the most reliable procedure involved preincubating the target cells with different dilutions of the unconjugated monoclonal antibody for 60 min at 4° C. followed by the addition of the optimal concentration of the toxin-linked univalent fragment for 36 h at 37° C. When cells expressed a high density of the target antigen, the primary antibody could be washed away before adding the toxin-linked univalent fragment without changing the $IC_{50}$ However, when the density of the target antigen was low, better reproducibility was obtained by eliminating the washing step. This may due to the requirement of repeated rounds of internalization of the 1° and 2° reagents when the cell surface antigen is expressed at a low density;

(c) when the washing step between the addition of the monoclonal antibody and the immunotoxin was omitted, a reduced cytotoxic effect was observed at the highest concentration of monoclonal antibody added to the cells. Although the reasons for this were not determined, it is likely that excess unbound 1° antibody complexed with the toxin-linked univalent fragment, thus inhibiting it from binding to the cell-bound antibody. Nevertheless, the $IC_{50}$ value was unchanged. It was, therefore, important to titrate the 1° monoclonal antibody rather than to use it at a single concentration. When using hybridoma supernatants, dilutions of 0.5, 0.1, and 0.01 proved to be sufficient;

(d) when some target cells were used in the indirect immunotoxin assay, the cells could be harvested 24 h after adding the primary antibody and the secondary immunotoxin. However, with other cells, 24 h did not give optimal results. In these cases, 36 h was found to give $IC_{50}$ values which were more reproducible and which more closely matched those obtained with 1° cells/well in either killing assay. When larger numbers of rapidly dividing cells were used as target cells, they gave high background killing values, presumably because they overgrew the wells and died during the 36 h of incubation.

EXAMPLE I

MATERIALS AND METHODS

Antibodies

Fourteen antibodies were used in this study. All were purified immunoglobulins. Their specificity and isotype are listed in Table 1. Goat anti-mouse immunoglobulin (GAMIg) was prepared by immunizing a goat with 100 ug of purified mouse serum IgG. The goat was boosted twice a year and bled at bimonthly intervals. Serum was affinity purified on a column of Sepharose-mouse serum immunoglobulin at a ratio of 1 ml Sepharose/10 ml serum. The bound GAMIg was eluted in 3.5 M $MgCl_2$, and vacuum dialyzed/concentrated to 1.0 mg/ml. Samples were stored at $-70°$ C.

TABLE 1

ANTIBODIES

All antibodies are of mouse origin with the exception of OX7 (rat), and goat anti-mouse immunoglobulin antibodies and were used as purified immunoglobulins or as tissue culture supernatants (SNS)

| Antibody | Class | Specificity | Ref. |
|---|---|---|---|
| 9.6 | IgG2a | Human CD2 | 30,31 |
| RFT11 | IgG1 | Human CD2 | 32 |
| 64.1 | IgG2a | Human CD3 | 30,31 |
| RFT1 | IgG1 | Human CD5 | 32 |
| RFT2a | IgG2a | Human CD7 | 32 |
| WT1 | IgG2a | Human CD7 | 33 |
| RFT8 | IgG1 | Human CD8 | 32 |
| R10 | IgG1 | Human glycophorin | 34 |
| OX7 | IgG1 | Thy-1.1 | 35 |
| UV22-1 | IgG1 | Human CD22 | Footnote 5 |
| UV22-2 | IgG1 | Human CD22 | Footnote 6 |
| HD6 | IgG1 | Human CD22 | 36 |
| RFB4 | IgG1 | Human CD22 | 32 |
| MOPC-21 | IgG1 | Unknown | Litton Bionetics, Kensington, MD |
| Anti-mouse immunoglobulin (goat) | Polyvalent | Mouse immunoglobulin | See "Materials and Methods" |

Cell Lines

Direct and indirect immunotoxin assays were performed on a panel of cell types (described below in Table 2). Cells were maintained in RPMI 1640 containing 10% fetal calf serum and antibiotics.

TABLE 2

Cell LINES

| Cell Line | Description |
|---|---|
| Daudi | Human Burkitt's lymphoma cell line. |
| EL-4 | Mouse thymoma cell line originating in a C57BL/6 mouse. |
| AKR-A | T-cell lymphoma cell line originating in an AKR mouse. |
| AKR-110 | T-cell lymphoma cell line originating in an AKR mouse (P. Krammer, Heidelberg, Germany). |
| Jurkat | Human T-cell leukemia cell line. |
| Nalm-6 | Pre-B-cell line established from a patient with acute lymphocytic |
| Chinese hamster ovary | Cell line initiated from biopsy of an ovary of an adult chinese hamster. This cell line was obtained from ATCC (Rockville, MD). |
| Peripheral blood T-cells | Obtained from human peripheral blood as described (37). |

Preparation of Toxin-Linked Fab Fragment

Fab fragments of affinity-purified GAMIg were prepared by papain digestion as described in reference 22 and were then reduced with 5 mM dithiothreitol for 1 hr at 25° C. and desalted on Sephadex G-25. The reduced fragments were reacted with a 100-fold M excess of 5,5'dithiobis(2-nitrobenzoic acid) (Ellman's reagent) (23) to convert the thiol groups of the cysteine residues into activated disulfide groups (24).

Ricin A chain (purchased from Inland Laboratories, Austin, TX) was purified and characterized as previously described (25). A chain was reduced with 5 mM dithiothreitol and coupled to the Ellman's-substituted Fab fragments as described (24). The reaction mixture was filtered through a column ($2.5 \times 80$ cm) of Sephacryl S-200. The univalent immunotoxin peak was collected and contaminating unconjugated Fab was removed by chromatography on Blue Sepharose column with 0.05 M $NaPO_4$ and 1 M NaCl, pH 7.0. The univalent immunotoxin was concentrated to 105 mg/ml, divided into sterile aliquots, and stored at $-20°$ C.

Preparation of Direct Immunotoxins

Antibodies were coupled to ricin A chain by means of one of three different disulfide cross-linking agents: 2-iminothiolane hydrochloride (27); N-succinimidyl-3-(2-pyridyldithio)propionate (28); or 4-succinimidyloxcarbonyl-a-methyl-a(2-pyridyldithio)toluene (29). The conjugation and purification procedures were as previously described (24, 27-29). The three coupling agents give immunotoxins of equal cytotoxic potency in vitro (27-29).

Indirect Immunotoxin Assay

Cells were used in logarithmic growth phase, where cell viabilities were greater than 95%. Serial dilutions of 1° unconjugated antibody ranging in concentration from $2 \times 10^{-8} - 2 \times 10^{-13}$M were prepared in the appropriate media and 100-ul aliquots were plated in triplicate in 96-well plates; $10^5$ cells in a volume of 100 ul of the same medium were added to each well and plates were incubated for 1 h at 4° C. Toxin-linked Fab fragments of goat anti-mouse immunoglobulin (Fab-GAMIg-A) at a final concentration of 2 ug/ml, was then added to the appropriate wells. Controls included (a) untreated cells, (b) cells treated with 2° immunotoxin only, (c) cells treated with 1° antibody only, and (d) cells treated with 1° antibody followed by Fab-GAMIg (no A chain). The plates were then incubated for 36 h at 37° C. in 5% $CO_2$. Cells were washed, resuspended in leucine-free medium, and pulsed for 4-8 h at 37° C. with 5 uCi of [$^3$H]leucine in the same medium. Cells were harvested on glass fiber filters using a Titertek automatic harvester. Incorporation of [$^3$H]leucine was determined by liquid scintillation counting in a LKB beta counter. Results were expressed as a percentage of the [$^3$H]leucine incorporated by the untreated cells. Cells in all the control cultures incorporated 80-100% of the [$^3$H]leucine taken up by untreated cells.

Direct Immunotoxin Assay

Cells suspended in RPMI 1640 medium supplemented with 10% fetal calf serum and antibiotics were distributed at $10^5$ cells/well in 96-well microtiter plates. Solutions of immunotoxins in the same medium were then added in triplicate, giving a final concentration of immunotoxin ranging from $10^{-7} - 10^{-13}$M. The plates were incubated for 36 h at 37° C. in an atmosphere of 5% $CO_2$ in humidified air. The cells were then washed, resuspended in leucine-free medium, and pulsed for 4-8 h with 5uCi/well [$^3$H]leucine. Cells were harvested as described above and their radioactivity was measured. Results were expressed as a percentage of the mean [$^3$H]leucine incorporation of 12-24 wells of untreated cells.

Immunofluorescence Analysis

The specificity of each antibody for the cell lines tested was evaluated by an indirect immunofluorescence assay; $10^6$ cells were treated with optimal concentrations of 1° monoclonal antibody (5–0.1 ug/ml) for 30 min at 4° C. After Washing with phosphate-buffered saline containing 10 mM sodium azide, the cells were incubated with fluorescein isothiocyanate-coupled GAMIg for 15 min at 4° C. Cells were washed and analyzed on a fluorescence activated cell sorter (FACSTAR; Becton Dickinson, Mountain View, Calif.). The percentage of positive cells and their mean fluorescence intensity are summarized below in Table 3.

TABLE 3

Indirect fluorescence analysis of cell lines stained with antibody and fluorescein isothiocyanate GAMIg

| Cell | Antibody | Specificity | % positive | Mean fluorescence intensity[a] |
|---|---|---|---|---|
| Daudi | HD6 | CD22 | 92.4 | 765 |
| | UV22-1 | CD22 | 97.1 | 982 |
| | UV22-2 | CD22 | 90.8 | 541 |
| | RFB4 | CD22 | 85.9 | 629 |
| | MOPC-21 | Unknown | 1.2 | 50 |
| EL-4 | R10 | Human glycophorin | 2.1 | 60 |
| | OX7 | Thy-1.1 | 0.9 | 17 |
| AKR-A | R10 | Human glycophorin | 1.2 | 55 |
| | OX7 | Thy-1.1 | 98.5 | 862 |
| AKR-110 | R10 | Human glycophorin | 0.1 | 25 |
| | OX7 | Thy-1.1 | 99.8 | 2484 |
| Chinese hamster ovary | R10 | Human glycophorin | 0.3 | 25 |
| | OX7 | Thy-1.1 | 0.1 | 26 |
| PBL T (human) | RFT11 | CD2 | 96.0 | 416 |
| | 9.6 | CD2 | 95.0 | 415 |
| | 64.1 | CD3 | 94.0 | 491 |
| | RFT1 | CD5 | 90.1 | 616 |
| | RFT2a | CD7 | 83.0 | 387 |
| | WT-1 | CD7 | 81.0 | 323 |
| | RFT8 | CD8 | 52.0 | 498 |
| | OX7 | Thy-1.1 (mouse) | 3.3 | 16 |
| Jurkat | RFT11 | CD2 | 99.2 | 639 |
| | RFT1 | CD5 | 99.3 | 448 |
| | RFT2a | CD7 | 95.9 | 448 |
| | WT-1 | CD7 | 98.2 | 652 |
| | RFT8 | CD8 | 3.6 | 21 |
| | OX7 | Thy-1.1 | 4.1 | 20 |
| Nalm-6 | UV22-1 | CD22 | 99.9 | 874 |
| | MOPC-21 | Unknown | 1.2 | 46 |

[a]Log scale maximum value = 10,000.

Comparison of the Direct and Indirect Assay

Data obtained from direct and indirect killing assays using coded samples indicated a correlation in $IC_{50}S$ between the two assays that approached 100%. The results of a typical comparison between an indirect and a direct assay are shown in FIG. 1 for the AKR-A cell line and the antibody, OX7 (anti-Thy-1). Comparisons of other cell lines, monoclonal antibodies, and immunotoxins are shown in tables 4–7.

TABLE 4

Comparison of $IC_{50}S$ of Immunotoxins on human pre-B and B-cells

| Target cell | Antibody | Specificity (Anti-) | $IC_{50} (\times 10^{-10}M)^a$ Indirect | Direct |
|---|---|---|---|---|
| Daudi | RFB4 | CD22 | 0.04 | 0.03 |
| | UV22-1 | CD22 | 0.5 | 0.3 |
| | UV22-2 | CD22 | 5.3 | 3.30 |
| | HD6 | CD22 | 1.5 | 1.3 |
| | OX7 | Thy-1.1 | >300 | >300 |
| | MOPC-21[b] | Unknown | >300 | >300 |
| Nalm-6 | UV22-1 | CD22 | 0.8 | 0.9 |

TABLE 4-continued

Comparison of $IC_{50}S$ of Immunotoxins on human pre-B and B-cells

| Target cell | Antibody | Specificity (Anti-) | $IC_{50} (\times 10^{-10}M)^a$ Indirect | Direct |
|---|---|---|---|---|
| | MOPC-21 | Unknown | >300 | >300 |

[a]Average of 3–7 separate experiments (SD among experiments was less than 30%).
[b]Myeloma protein. (control)

TABLE 5

Comparison of $IC_{50}S$ of Immunotoxins on mouse T-cell lymphoma or lines

| Cell line | Antibody | Specificity (Anti-) | $IC_{50} (\times 10^{-10}M)^a$ Indirect | Direct |
|---|---|---|---|---|
| AKR/A | OX7 | Thy-1.1 | 0.2 | 0.1 |
| | R10 | Human glycophorin | >300 | >300 |
| AKR-110 | OX7 | Thy-1.1 | 0.8 | 0.2 |
| | R10 | Human glycophorin | >300 | >300 |
| El-4 | OX7 | Thy-1.1 | >300 | >300 |
| | R10 | Human glycophorin | >300 | >300 |

[a]Average of 3–7 separate experiments (SD experiments was less than 30%).

TABLE 6

Comparison of $IC_{50}S$ of Immunotoxins on human peripheral blood T-cells and a T-cell leukemia

| Target cell | Antibody | Specificity (Anti-) | $IC_{50} (\times 10^{-10}M)^a$ Indirect | Direct |
|---|---|---|---|---|
| PBL T | 9.6 | CD2 | >300 | >300 |
| | RFT11 | CD2 | 2.0 | 1.0 |
| | 64.1 | CD3 | 0.3 | 0.6 |
| | RFT1 | CD5 | 5.0 | 0.8 |
| | RFTa | CD7 | 2.0 | 3.0 |
| | WT-1 | CD7 | 8.0 | 3.0 |
| | RFT8 | CD8 | >300 | >300 |
| | OX7 | Thy-1.1 | >300 | >300 |
| Jurkat | RFT11 | CD2 | 0.5 | 0.1 |
| | RFT1 | CD5 | >300 | >300 |
| | RFT2a | CD7 | 1.6 | 0.3 |
| | WT-1 | CD7 | 1.0 | 0.03 |
| | RFT8 | CD8 | >300 | >300 |
| | OX7 | Thy-1.1 | >300 | >300 |

[a]Average of 3–7 separate experiments (SD among experiments was less than 30%).

TABLE 7

Comparison of $IC_{50}S$ of Immunotoxins on Chinese hamster ovary cell lines

| Cell line | Antibody | Specificity (Anti-) | $IC_{50} (\times 10^{-10}M)^a$ Indirect | Direct |
|---|---|---|---|---|
| Chinese hamster ovary | R10 | Human glycophorin | >300 | >300 |
| | OX7 | Thy-1.1 | >300 | >300 |

[a]Average of 3–7 separate experiments (SD was less than 30%).

As can be seen in Tables 4–7, the $IC_{50}S$ obtained from the direct and indirect assays were generally within 5-fold of each other. Using the panel of monoclonal antibodies and immunotoxins described here, the presence of positively stained cells and a high mean fluorescence intensity generally indicated that an immunotoxin specific for a given antigen would be toxic. However, the $IC_{50}$ did not correlate directly with the density of the cell surface antigen. In an extreme case, such as 9.6 (anti-CD2) on PBL T-cells (Table 6), there was no killing in either the indirect or the direct assay, even though the cells were positive by immunofluorescence (Table 3). These results indicate that the route of internalization of some antigens, and not their density, is critical in determining whether they will serve as good targets for immunotoxin therapy. This has been indicated by Press et al. (30,31) who reported that antigen-immunotoxin complexes that are routed to endosomes are effective immunotoxins, while those routed to lysosomes are not.

In other cases, the cell type determines the efficacy of a monoclonal antibody as an immunotoxin, e.g., RFT-1 (anti-CD5) on Jurkat versus PBL T-cells. In the former instance, the monoclonal antibody or immunotoxin is not toxic, while in the latter it is (Table 6). Surprisingly, the density of the antigen on Jurkat cells is only one-half that on PBL T-cells (Table 3).

Figure 2:
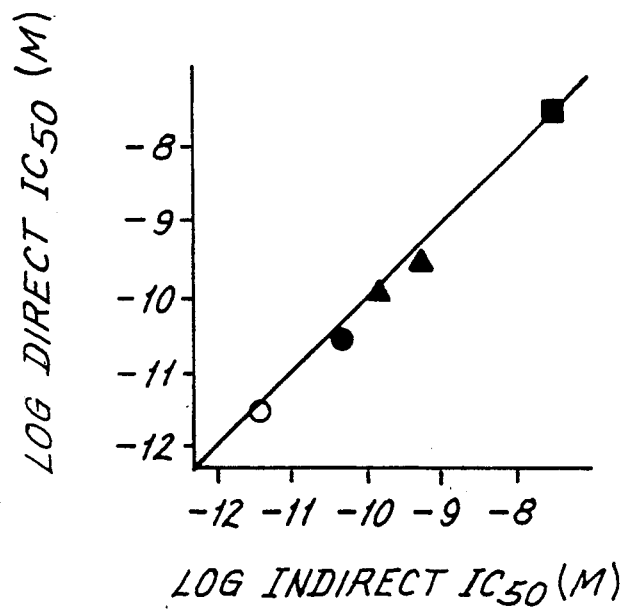

FIG. 2 shows the correlation between the $IC_{50}$ obtained in the indirect versus direct killing assay using a single cell line (Daudi) and several anti-CD22 antibodies, all of which gave similar staining patterns As emphasized in the FIG. 2, the indirect assay predicted that antibodies with the same specificity, namely, anti-CD22, would differ by greater than 2 logs in their efficacy as immunotoxins and this was confirmed by the direct immunotoxin assay. The effectiveness of the anti-CD22 antibodies as immunotoxins correlated to some extent with both their functional affinity (avidity) as measured by Scatchard analysis and the epitope on the CD22 molecule which they recognize.

The correlation between the affinity of the antibody and its efficacy as an immunotoxin has been reported previously (17) and agrees with the results obtained from the anti-CD22 antibodies used in the present study. With respect to the epitope recognized by monoclonal antibodies, two monoclonal antibodies (or immunotoxins) with the same affinities but directed against different epitopes on the same molecule (RFT11 versus 9.6 anti-CD2) show marked differences in efficacy (Table 6) despite similar staining patterns (Table 1) (31) and affinities. Thus, the epitope on a molecule that a monoclonal antibody recognizes can determine its suitability as an immunotoxin. Those monoclonal antibodies recognizing epitopes closest to the membrane may be most effective. In summary, although many features of a monoclonal antibody and the cell surface epitope which it recognizes determine its efficacy as an immunotoxin, the results of the indirect assay accurately predict the toxicity of direct immunotoxin on the cell lines tested in this study.

The present invention demonstrates the development of a rapid, simple, and reproducible assay for predicting the potency of a monoclonal antibody as an immunotoxin in vitro. This assay should facilitate screening of monoclonal antibodies and thereby allow the selection of those that will make clinically useful immunotoxins. Using this indirect assay, the relative effectiveness of a panel of monoclonal antibodies coupled to ricin A chain was compared. The results indicated a correlation between the direct and indirect assays which was virtually 100% using 8 different target cells and 14 different monoclonal antibodies.

It is of importance that the indirect assay was effective in predicting differences in the direct assay resulting from (a) the affinity of the antibody, (b) the epitope on the cell surface molecule which the antibody recognized, and (c) differences in the cell type on which the molecule was expressed. It is also possible to apply this assay to supernatants of hybridoma cells after their selection for cell specificity and can therefore serve as an effective secondary screening assay for selecting monoclonal antibodies to be used as immunotoxins.

The present invention has been disclosed in terms of standard laboratory practices found by the present inventors to constitute preferred methods for practicing the invention. However, it will be apparent to those of skill in the art that modifications and changes may be made in the present invention without departing from the spirit and scope of the invention. Such modifications are intended to be within the scope of the invention as defined by the appended claims.

REFERENCES

The following references are hereby incorporated by reference.

1. Krolick et al., Selective killing of normal or neoplastic B cells by antibody coupled to the A chain of ricin. *Proc. Natl. Acad. Sci. USA*, 77:5419–5423, 1980.

2. Thorpe et al., Toxicity of diptheria toxin for lymphoblastoid cells is increased by conjugation to anti-lymphocytic globulin. *Nature* (Lond ), 271:752–754, 1978.

3. Blythman et al., Immunotoxins: hybrid molecules of monoclonal antibodies and a toxin subunit specifically kill tumor cells. *Nature* (Lond.), 290:145–147, 1981.

4. Youle et al., Anti-Thy-1.2 monoclonal antibody linked to ricin is a potent cell type-specific toxin. *Proc. Natl. Acad. Sci. USA*, 77:5483–5486, 1980.

5. Krolick et al., In vivo therapy of a murine B cell tumor ($BCL_1$) using antibody-ricin A chain immunotoxins. *J. Exp. Med.*, 155:1797–1809, 1982.

6. Jansen et al., High specific toxicity of antibody-toxin hybrid molecules (immunotoxins) for target cells. *Immunol. Lett.*, 2:97–102, 1980.

7. Kishida et al., Ricin A chain conjugated with monoclonal anti-L1210 antibody. In vitro and in vivo anti-tumor activity. *Cancer Immunol. Immunother.*, 16:93–97, 1983.

8. Fitzgerald et al., Anti-tumor effects of an immunotoxin made with pseudomonas exotoxin in a nude mouse model for human ovarian cancer. *Proc. Natl. Acad. Sci. USA*, 83:6627–6630, 1986.

9. Hara et al., Complete suppression of in vivo growth of human leukemia cells by specific immunotoxins: nude mouse models. *Proc. Natl. Acad. Sci. USA*, 84:3390–3394, 1987.

10. Vitetta et al., Redesigning nature's poisons to create anti-tumor reagents. *Science (Wash. D.C.)*, 238:1098–1104, 1987.

11. Blakey et al., Antibody toxin, conjugates: a perspective. *Prog. Allergy*, 45:50–90, 1988.

12. Casellas et al. Human melanoma cells can be killed in vivo by an immunotoxin specific for melanoma-associated antigen. *Int. J. Cancer*, 30:437–443, 1982.

13. Press et al., Evaluation of ricin A chain immunotoxins directed against human T cells. *Cell. Immunol.*, 102:10–20, 1986.

14. Lambert et al., Purified immunotoxins that are reactive with human lymphoid cells. *J. Biol. Chem.*, 260:12035–12041, 1985.

15. Griffin et al., Selective toxicity of ricin A chain anti CEA conjugates to human adenocarcinoma cells. In: G. Gregoriadis, G. Poste, J. Senior and A. Trouet (eds), Receptor-Mediated Targeting of Drugs, pp. 187–200. New York: Plenum Press, 1984.

16. Embleton et al., Sensitivity and selectivity of ricin toxin A chain monoclonal antibody 791T/36 conjugates against human tumor cell lines. *Cancer Res.*, 46:5524–5528, 1986.

17. Ramakrishnan et al., Comparison of the selective cytotoxic effects of immunotoxins containing ricin A chain or pokeweed antiviral protein and anti-Thy-1.1 monoclonal antibodies. *Cancer Res.*, 44:201–208, 1984.

18. Bjorn et al., Evaluation of monoclonal antibodies for the development of breast cancer immunotoxins. *Cancer Res.*, 45:1214–1221, 1985.

19. Raso et al., Monoclonal antibody-ricin A chain conjugate selectively cytotoxic for cells bearing the common acute lymphoblastic leukemia antigen. *Cancer Res.*, 42:457–464, 1982.

20. Weltman et al., Indirect immunotoxin method for demonstrating antibodies against human tumor cells. *Biotechniques*, 4:224–228, 1986: Weltman, U.S. Pat. No. 4,689,311, issued Aug. 25, 1987.

21. Metezeau et al., Endocytosis of the membrane immunoglobulins of mouse spleen B cells: a quantitative study of its rate, amount and sensitivity to physiological physical and cross-linking agents. *EMBO J.*, 3:2235–2238, 1984.

22. Fanger et al., Enhancement by reducing agents of the transformation of human and rabbit peripheral lymphocytes. *J. Immunol.*, 105:1043–1045, 1970.

23. Ellman, Tissue sulfhydryl groups. *Arch. Biochem. Biophys*, 82:70–77, 1959.

24. Fulton, et al., The effect of antibody valency and lysosomotropic amines on the synergy between ricin A chain-and ricin B chain-containing immunotoxins. *J. Immunol.*, 136:3103–3109, 1986.

25. Fulton et al., Purification of ricin A1, A2 and B chains and characterization of their cytotoxicity. *J. Biol. Chem.*, 261:5314–5319, 1986.

26. Knowles et al., Purification of immunotoxins containing ricin A chain and abrin A chain using Blue Sepharose CL-6B. *Anal Biochem.*, 160:440–443, 1987.

27. Thorpe et al., The preparation of cytotoxic properties of antibody-toxin conjugates. *Immunol. Rev.*, 62:119–158, 1982.

28. Thorpe et al., Comparison of two anti-Thy-1.1 abrin A chain immunotoxins prepared with different cross-linking agents: anti-tumor effects, in vivo fate, anti-tumor cell mutants, *J. Natl. Cancer Inst.*, in press, 1987.

29. Thorpe et al., New coupling agents for the synthesis of immunotoxins containing a hindered disulfide bond with improved stability in vivo. *Cancer Res.*, 47:5924–5931, 1987.

30. Press et al., Evaluation of ricin A chain immunotoxins directed against human T cells. *Cell. Immunol*, 102:10–20, 1986.

31. Press et al., Ricin A-Chain containing immunotoxins directed against different epitopes on the CD2 molecules differ in their ability to kill normal and malignant T cells. *J. Immunol.*, in press.

32. Campana et al., Human B cell development. I. Phenotypic differences of B lymphocytes in the bone marrow and peripheral lymphoid tissue *J. Immunol.*, 134:1524–1530, 1984.

33. Tax et al., Monoclonal antibody (WT-1) directed against a T cell surface glycoprotein: characteristics and immunosuppressive activity. *Clin. Exp. Immunol.*, 55:427–436, 1984.

34. Robinson et al., Expression of cell surface HLA-DR, HLA-ABC and glycophorin during erythroid differentiation. *Nature (Lond.)*, 289:68–71, 1981.

35. Mason et al., The kinetics of antibody binding to membrane antigens in solution and/or the cell surface. *Biochem. J.*, 187:1–20, 1980.

36. Dorken et al., B cell differentiation antigens identified by monoclonal antibodies (HD6, HD28, HD37, HD39). *Immunobiology*, 165:253–257, 1983.

37. Rosenberg et al., Monocyte dependence of pokeweed mitogen-induced differentiation of immunoglobulin-secreting cells from human peripheral blood mononuclear cells. *J. Immunol.*, 122:926–930, 1979.

38. Weltman et al., Rapid screening with indirect immunotoxin for monoclonal antibodies against human small cell lung cancer. *Cancer Res.*, 47:5552–5556, 1987.

What is claimed is:

1. An in vitro method for assessing the ability of an antibody selected from a group of antibodies to deliver a toxin to a selected target cell, the method comprising the steps of:
   (a) incubating target cells with an antibody to be so assessed in an aqueous mixture under conditions appropriate for immunocomplex formation;
   (b) introducing into the incubation mixture a toxin convalently linked to a univalent antibody fragment, said fragment having binding affinity for said antibody;
   (c) assessing the ability of said antibody to deliver the toxin; and
   (d) comparing the toxin-delivering ability of said antibody to the toxin-delivering ability of another member of the group of antibodies to select an antibody having the desired toxin-delivering ability.

2. The method of claim 1 wherein the univalent antibody fragment comprises an Fab fragment.

3. The method of claim 1 wherein the toxin comprises an A chain toxin.

4. The method of claim 3 wherein the A-chain toxin comprises ricin A chain.

5. The method of claim 1 wherein the target cell comprises a tumor cell.

6. The method of claim 1 wherein the antibody comprises a monoclonal antibody.

7. The method of claim 1 wherein step (c) comprises testing for an inhibition of protein synthesis in the target cells.

8. The method of claim 1, wherein the antibody to be so assessed comprises an antibody having affinity for a tumor cell, B-cell or T-cell epitope.

9. The method of claim 8, wherein the antibody to be so assessed comprises one having affinity for an antigen selected from the group of antigens consisting of CD2; CD3; CD5; CD7; CD8; human glycophorin; Thy-1.1; and CD22.

10. In an in vitro method for assessing the ability of an antibody to deliver a toxin to a selected target cell which includes incubating target cells in an admixture which includes a first antibody and a toxin convalently linked to a second antibody having immunospecificity for the first antibody, wherein the improvement comprises:
   employing a toxin convalently linked to a univalent antibody fragment in place of said toxin convalently linked to a second antibody.

* * * * *